United States Patent

Sampsell et al.

Patent Number: 5,327,286
Date of Patent: Jul. 5, 1994

[54] REAL TIME OPTICAL CORRELATION SYSTEM

[75] Inventors: Jeffrey B. Sampsell, Plano; Rachelle J. Bienstock, Dallas, both of Tex.

[73] Assignee: Texas Instruments Incorporated, Dallas, Tex.

[21] Appl. No.: 937,987

[22] Filed: Aug. 31, 1992

[51] Int. Cl.$^5$ .......................... G02B 27/46; G02B 9/64
[52] U.S. Cl. ..................................... 359/561; 359/559; 382/42; 382/43
[58] Field of Search ......................... 359/559, 561, 560; 382/31, 42, 43

[56] References Cited

U.S. PATENT DOCUMENTS

| | | | |
|---|---|---|---|
| 4,659,172 | 4/1987 | Cavan | 359/33 |
| 4,712,851 | 12/1987 | Fusek et al. | 359/1 |
| 4,806,774 | 2/1989 | Lin et al. | 250/550 |
| 4,811,409 | 3/1989 | Cavan | 382/8 |
| 5,172,000 | 12/1992 | Scheff et al. | 250/550 |
| 5,216,541 | 6/1993 | Takesue et al. | 359/561 |

Primary Examiner—Scott J. Sugarman
Assistant Examiner—Darryl J. Collins
Attorney, Agent, or Firm—Julie R. Reed; James C. Kesterson; Richard L. Donaldson

[57] ABSTRACT

An optical correlation unit for correlating the images of an inspection object and a reference object. The unit uses two phase modulating reflective spatial light modulators. A first spatial light modulator receives electronic input in the form of image data representing the inspection object. It modulates incoming light with this input and reflects the modulated output to a first Fourier transform lens. This lens provides the optical input to a second spatial light modulator, whose electronic input is transform data representing the complex conjugate of the Fourier transform of the reference image. The electronic input modulates the optical input, resulting in the Fourier product of the two images, which is then transformed to provide correlation data.

18 Claims, 2 Drawing Sheets

REAL TIME OPTICAL CORRELATION SYSTEM

TECHNICAL FIELD OF THE INVENTION

This invention relates to optical inspection processes, and more particularly to an inspection system that compares an object under inspection with a reference image or object.

BACKGROUND OF THE INVENTION

One method of testing for defects in articles of manufacture is to compare the article with a desired image of the object or with another object that is known to be satisfactory. A typical example is the inspection of wafers to be used in semiconductor fabrication. A slice of a wafer in process is compared to a reference, which may be a reference slice of a known good wafer, or to a desired image.

Various methods of pattern comparison have been developed. Typically, correlation techniques are used, where a signal representing a reference image is compared to a signal representing the article under inspection. In an optical correlation system, the correlation peak, which indicates a match between two images, is represented by a bright point of light in the output light distribution.

For optical applications with coherent light, where lenses may be used to produce Fourier transform images, correlation systems are often based on Fourier optics. These systems involve optical operations on transform images, which may be expressed mathematically as functions, $f(x,y)$ and transform functions, $F(u,v)$. The Fourier transform of the correlation is the same as multiplication of the Fourier transform of one function by the complex conjugate of the Fourier transform of the other.

One conventional approach to coherent optical correlation of two images is the use of Fourier holograms along a 4f system. The 4f system is so called because the light follows a path along a single axis that is four times the focal length of the lenses used. A photographic hologram recording is made that represents the Fourier transform of a reference object's light distribution. The hologram acts as a spatial filter, whose transmittance is the complex conjugate of incoming light. Then when light representing a first function passes through the hologram, it is modulated by the complex conjugate of the function representing the image from which the hologram was made. This output light is inverse Fourier transformed by a second lens to provide the correlation output. If the images are matched, a bright spot appears.

One problem with holographic methods that use photographic holograms is that the hologram is fixed for a particular reference object. If the reference changes, another hologram must be generated, which is costly in terms of time and money.

Correlation with spatial light modulators provides an alternative to holographic methods that use photographic recordings. In effect, the spatial light modulator acts as a real time, programmable, hologram. In an exemplary system, an input image is Fourier transformed with a lens to a transform plane, where an LCD type of transmitting spatial light modulator represents a reference image. The total light transmitted through the spatial light modulator is again Fourier transformed to result in the transform product. Although an advantage of many spatial light modulators is their programmability, problems with using them arise from their low resolution and slow write-use-erase rates. Other difficulties arise because of the sensitivity of Fourier transform operations to scale and alignment differences between image planes.

Variations of the above described techniques include joint transform systems, in which two images are presented to two different input planes. Both are Fourier transformed by the same transform lens and their Fourier product falls on the same plane. However, these systems typically include photographic holograms or spatial light modulators as holographic filters and have the problems associated with the other systems described above.

A need exists for an optical correlation system that is programmable and can respond to a changing reference in real time.

SUMMARY OF THE INVENTION

One aspect of the invention is an optical correlation unit, which provides a correlation image from image data representing a first object and Fourier transform image data representing a second object. The correlation unit uses two spatial light modulators, having reflective, phase modulating elements. A first phase modulating spatial light modulator receives electronic input to each mirror element, which is image data representing one of the objects. This data controls the phase modulation by the mirror elements of light from a coherent source that illuminates the surface of the first spatial light modulator. A first Fourier transform lens receives light reflected from the surface of the first phase modulating spatial light modulator. A second phase modulating spatial light modulator receives electronic input that represents the transform of the second object. This second spatial light modulator is located at the Fourier image plane of the first Fourier transform lens. A beam splitter directs light reflected from the second spatial light modulator to a second Fourier transform lens. An image capture device located at the Fourier image plane of the second Fourier transform lens captures the correlation image.

One advantage of the invention is that one or both of the objects to be compared may be represented by stored image data. Alternatively, the image data for one or both of the objects may be obtained by viewing the objects in-situ.

In a typical application of the invention, an actual object is inspected in-situ by comparing its image data with that of a reference object. For this type of application, an image capture unit is used to obtain image data representing the object to be inspected. The object may be inspected in real time and its surface may be scanned part by part and compared with a reference object or with stored data represented by the reference object.

A technical advantage of the invention is that the inputs to the correlation unit are not optically connected to the objects under inspection or the reference object. Thus, the correlation unit can be physically remote, with only a data link for communicating the input data.

The phase encoding of the input data results in high efficiency, in terms of percent of the input signal energy that is concentrated at the correlation peak. Also, the use of a spatial light modulator to receive video data of the inspection object's image permits that data to be acquired from an inspection object that can have any shape and need not guarantee a good reflection of light.

DETAILED DESCRIPTION OF THE INVENTION

Figure 1:
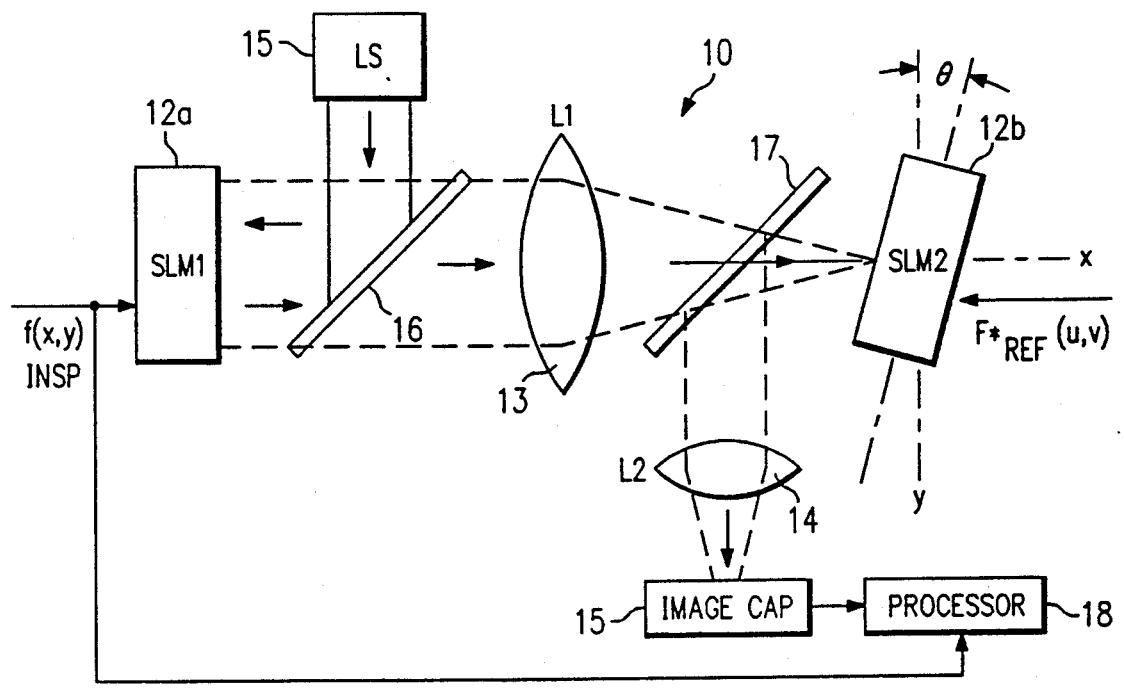
FIG. 1 illustrates an optical correlation unit in accordance with the invention.

FIG. 1 is a block diagram of an optical correlation unit 10 in accordance with the invention. One input to the system is image data, $f_{inspec}(x,y)$, which represents an object to be inspected. Another input to the system is Fourier transform data, $F^*_{ref}(u,v)$ which represents the complex conjugate of the Fourier transform of an image of a reference object. Both the image data and the transform data may come from a stored data source or from real time image data acquisition. By "real time" is meant that the correlation process can be performed as the actual objects to be compared are viewed. It is also possible that one set of input data could be from a stored source and another set from real time data acquisition. Data acquisition units for obtained image data and transform data are explained below in connection with FIGS. 3 and 4.

For purposes of FIG. 1, it is assumed that the image data and transform data have a common reference point that can be used to align them. A motion stage for aligning an inspection object and a reference object is discussed below in connection with FIG. 5.

The system of FIG. 1 includes two deformable micromirror spatial light modulators 12a and 12b. An underlying premise of the invention is that these spatial light modulators (SLMs) 12a and 12b may be used to provide phase modulated images for correlation purposes. Each SLM12 has an electrical input, which is used to modulate an optical input.

As an overview of operation of the invention, the inspection object's image data, $f_{inspec}(x,y)$, is input to a first SLM 12a, which outputs a phase modulated image of the inspection object. This image is Fourier transformed with a first transform lens 13, using the known property of lenses that provides a Fourier transform of an image when an image plane is one focal length from a lens. The resulting transform image illuminates the surface of a SLM 12b. At the same time, SLM 12b is phase modulated in accordance with Fourier transform data, $F^*_{ref}(u,v)$ from a reference image. The resulting reflection from the surface of the SLM 12b is the product of the two Fourier transformed images. This reflection is again Fourier transformed with a transforming lens 14 to result in a correlation image.

Figure 2:
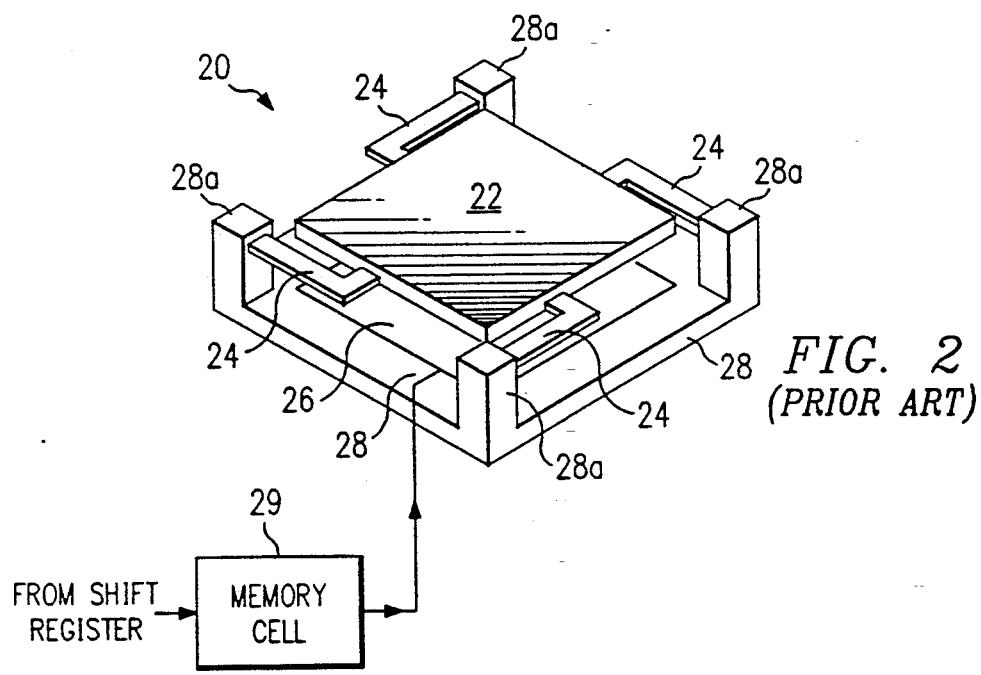
FIG. 2 illustrates a deformable micro-mirror device, such as used in the correlation unit of FIG. 1.

FIG. 2 illustrates an example of a mirror element 20 of a phase modulating SLM, suitable for use in the correlation unit 10. At each mirror element 20, the position of a mirror 22 determines the phase of light deflected from its surface back to an image plane.

SLM's having mirror elements 20 like those of FIG. 2 are commonly known as deformable micro-mirror devices (DMDs). However, any other type of reflective, phase modulating SLM could be used. In general, a reflective phase modulating SLM operates by adjusting individual pixel elements, such that light reflected from the SLM is encoded into phase modulated pixel beams.

The example of FIG. 2 is a flexure beam mirror element 20, a special version of those used in "cantilever" type DMDs. A rigid mirror 22, which can be any reflective flat surface, is supported by four hinges 24. Due to the square arrangement of cantilever hinges 24 at right angles to each other, mirror 22 is capable of up and down motion. For providing the motion, an electrode 26 is located under each mirror 22, spaced away from the mirror 22. Each electrode 26 is individually addressable with an applied voltage via an electrical input line 27. A memory cell 29 associated with each mirror element 20 stores a desired applied voltage state and permits all mirror elements 20 of a DMD to be simultaneously adjusted.

When a pre-determined voltage is applied to electrode 26, mirror 22 is electrostatically attracted to it. Hinges 24 permit mirror 22 to move downward toward electrode 26, for a distance that can be determined by the amount of applied voltage. When the applied voltage is removed, hinges 24 provide a restoring force to reset mirrors 22 to a zero phase change state.

An SLM 12a or 12b having the mirror elements 20 of FIG. 2 may be fabricated using integrated circuit techniques. For ease of fabrication, mirror 22 may be built over a spacer layer 28. The spacer material may be etched away to leave four support posts 28a with a gap between electrode 26 and mirror 22.

Referring again to FIG. 1, illumination for SLM 12a is provided from a coherent light source 15 such as a laser. This light is directed to SLM 12a via a beam splitter 16. SLM 12a receives electronic input data, $f_{inspec}(x,y)$, which it uses to modulate the light incident on its surface from source 15. The output image reflected from SLM 12a is a phase encoded image of the inspection object. In effect, SLM 12a converts the amplitude modulated inspection image to a phase modulated image.

The phase encoded image from SLM 12a passes through beam splitter 16 and through a first Fourier transforming lens 13. The transform image appears on the surface of SLM 12b, which is at one focal length from lens 13, i.e., at the Fourier image plane. The result is that the optical input to SLM 12b is the Fourier transformed image of the inspection object, $F_{inspec}(u,v)$.

The electronic input to SLM 12b is transform data, $F^*_{ref}(u,v)$, which represents the complex conjugate of the transform image of the reference object. SLM 12b modulates the optical input with the electronic input. In mathematical terms, the reflected output of SLM 12b can be expressed as the product of the two transform functions:

$$F_{inspec}(u,v) \times F^*_{ref}(u,v).$$

Of course, either of the above Fourier functions may be multiplied by the complex conjugate of the other for the same result, thus in an alternative embodiment of the invention, $F^*_{inspec}(u,v)$ could be multiplied by $F_{ref}(u,v)$.

The output light reflected from SLM 12b is directed out of the path of the incoming light from Fourier transform lens 13 by means of beam splitter 17. This redirected light is transformed by a second Fourier transforming lens 14, which has an image capture device 15 at its focal point.

The image data received at image capture device 15 can be expressed mathematically as:

$$F[F^*_{ref}(u,v) \times F_{inspec}(u,v)],$$

where the outer transform operation results in an inverted correlation image. The product is a four-term value, one term of which represents correlation data. The other terms represent convolution and zero order data, which can be filtered out using known optical filtering techniques.

In the preferred embodiment, SLM 12b is slightly tilted with respect to the image plane from lens 13. In FIG. 1, this angle is represented by the angle $\theta$, between an y axis orthogonal to an x axis (image path) and the cross sectional axis of SLM 12b. As a result, the image represented by the correlation term is spatially offset from the images resulting from the zero order and convolution terms at image capture unit 15. Thus, a bias term appears in the modulating function, which introduces a linear phase difference in the four product terms.

If desired, the inspection image data, $f_{inspec}(x,y)$, can be communicated to processing unit 18 as well as to SLM 12a. The image data could then be used by processing unit 18 to provide an image on a display or printer, upon which correlation data can be superimposed to indicate the exact location of a defect.

Figure 3:
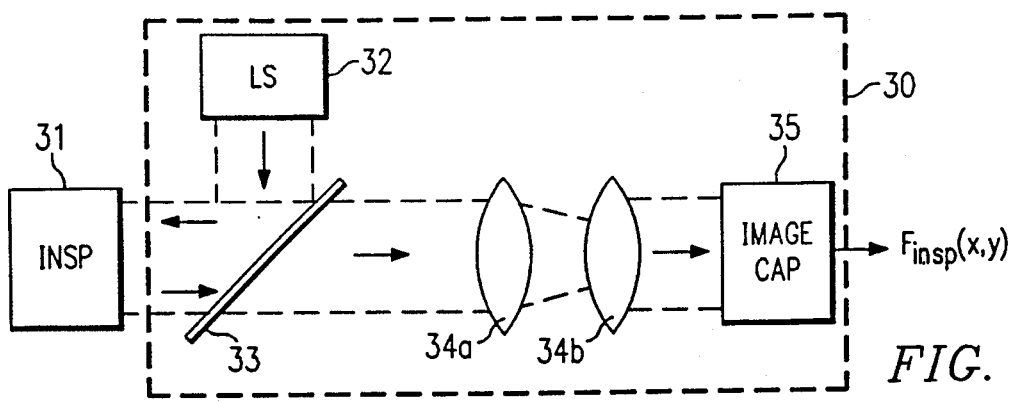
FIG. 3 illustrates an image capture unit for providing data representing the object to be inspected.

FIG. 3 illustrates an input data acquisition unit 30 for acquiring the image data, $f_{inspec}(x,y)$, which represents an inspection object 31. An image of inspection object 31 is formed by illuminating it with light from a source 32. Typically, a source 32 that produces a white or monochromatic non-coherent light will be used to prevent speckle effects. A beam splitter 33 reflects part of the light from source 32 to the inspection object 31, which then reflects light through beam splitter to lenses 34a and 34b. Lenses 34a and 34b form an image on an electronic image capture device 35. In the preferred embodiment, image capture device 35 is a charge coupled device (CCD), but any one of a number of known image capture devices may be used. Image capture device 35 generates electronic data, $f_{inspec}(x,y)$, representing an amplitude encoded image of inspection object 31. As shown in FIG. 1, this data is communicated to SLM 12a, which converts its to phase encoded data.

Figure 4:
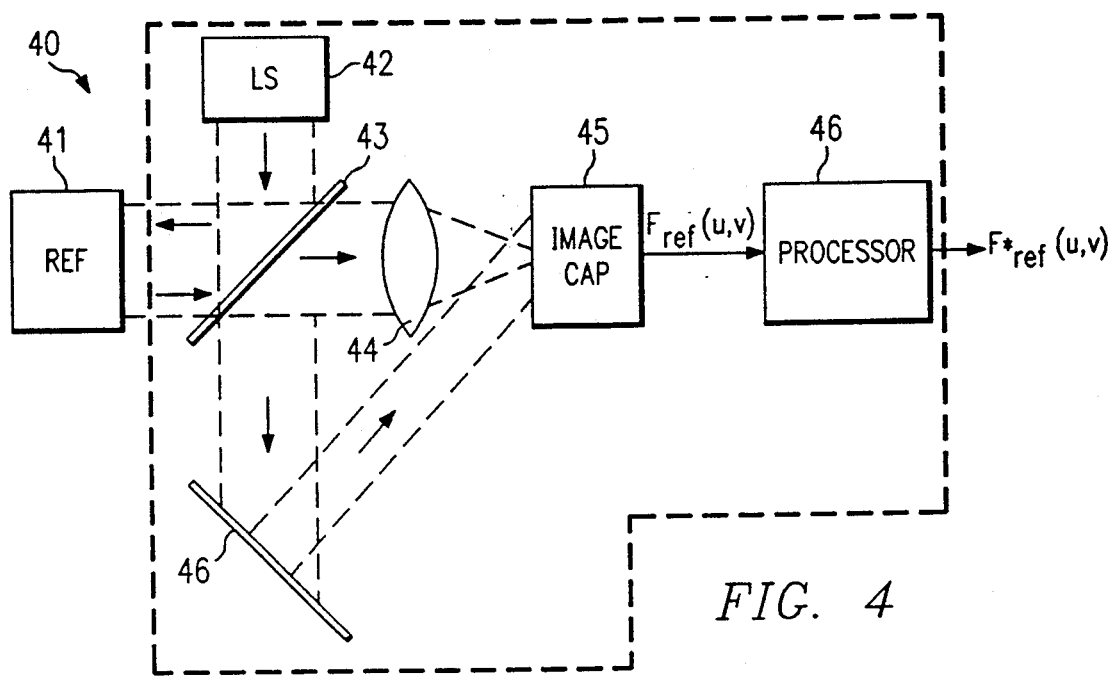
FIG. 4 illustrates an image capture unit for providing transform data representing a reference object.

FIG. 4 illustrates a reference data acquisition unit 40 for acquiring data, $F_{ref}(u,v)$, which represents the transform image of the reference object 41. Reference object 41 is assumed to be capable of providing a phase modulated image. The type of reference object 41 that may be used will depend on the application. For example, for a wafer inspection application, a reticle of an integrated circuit could be used as reference object 41. An actual three dimensional object could be used if it provides a phase modulated image.

Reference object 41 is illuminated with coherent light from source 42. Coherent light is used because reference object 41 is typically a coherent image. However, for noncoherent reference objects 41, a non-coherent source could be used. In the preferred embodiment, coherent source 42 is a laser with a beam expander (not shown).

A beam splitter 43 passes light from source 42 to illuminate reference object 41. It also permits reflected light from the reference object 41 to travel to Fourier transforming lens 44. Lens 44 produces a Fourier transform of the reference image on image capture device 45.

A mirror 46 receives light from source 42, which it reflects to image capture device 45. This reflected light is off axis from the reference image data. It provides a reference beam, so that phase information can be extracted from the Fourier image. The image data detected by image capture unit 45 can be expressed as $F_{ref}(u,v)$. Like image capture device 35, image capture device 45 is preferably a CCD.

The Fourier transform image from image capture device 45 is processed to provide its complex conjugate. This processing may be performed by any dedicated or general processing device 47, which may be processor 18. An electronic signal representing the transform image, $F^*_{ref}(u,v)$, is communicated to SLM 12b.

Figure 5:
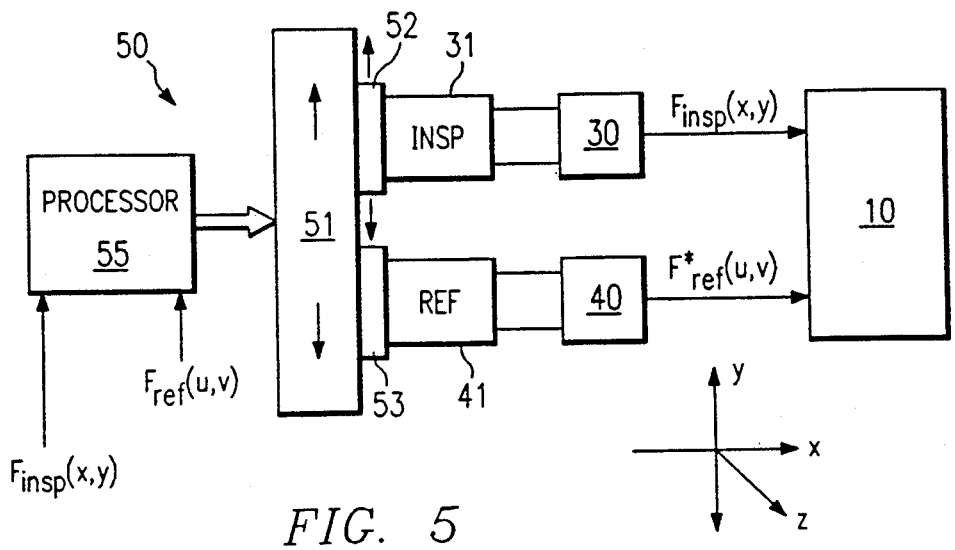
FIG. 5 illustrates a motion stage for aligning the object to be inspected and a reference object.

FIG. 5 illustrates a motion stage 50, for aligning inspection object 31 and reference object 41 and for permitting large objects to be inspected, portion by portion. In FIG. 1, the inspection object image and reference object transform image are assumed to be aligned, such that the point of focus of the transform images are matched at lens 14.

A motion stage 51 is moveable in at least one direction, such that either the length or width of the inspection and reference objects 31 and 41 can be scanned within the view of their image capture units 30 and 40. The motion stage 50 is used to sight the center of reference object 41 at the center of image capture unit 40.

Platforms 52 and 53 hold the inspection object and the reference object 31 and 41, respectively. One of the platforms, which is platform 52 in FIG. 5, is moveable with respect to motion stage 50 for alignment purposes.

In operation, processor 55 receives the video output of image capture devices 35 and 45. This data is used to control the motion of platform 52 so that the images from objects 31 and 41 are bore-sighted on image capture units 30 and 40. Once this alignment is achieved, motion stage 50 can be moved in the y-3 plane to inspect any selected portion of object 31.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An optical correlation unit for providing a correlation image from image data representing a first object and Fourier transform image data representing a second object, comprising:
   a first phase modulating spatial light modulator, having an array of reflective elements and means for receiving electronic input to each reflective element, wherein said electronic input represents a point of an input image and controls the phase modulation by said reflective; element of light incident on its surface;
   a coherent light source for illuminating the surface of said reflective elements of said first spatial light modulator;
   a first Fourier transform lens for receiving light reflected from the surface of said first phase modulating spatial light modulator;

a second phase modulating spatial light modulator, having an array of reflective elements and having means for receiving electronic input to each reflective element, wherein said electronic input represents a point of an input image and that controls the phase modulation by said reflective element, and wherein said second phase modulating spatial light modulator is located at the Fourier image plane of said first Fourier transform lens;

means for directing light reflected from said second spatial light modulator to a second Fourier transform lens;

a second Fourier transform lens for receiving said light reflected from said second spatial light modulator; and an image capture device located at the Fourier image plane of said second Fourier transform lens.

2. The optical correlation unit of claim 1, wherein said second spatial light modulator is tilted at an angle with respect to the image plane of said first Fourier transform lens.

3. The optical correlation unit of claim 1, wherein at least one of said spatial light modulators is a deformable micro-mirror device.

4. The optical correlation unit of claim 1, wherein said means for directing light is a beam splitter.

5. The optical correlation unit of claim 1, wherein each said spatial light modulator modulates light incident at its surface by adjusting the position of said reflective elements so as to change the path length of incoming light to an image plane.

6. The optical correlation unit of claim 1, wherein image data is obtained by viewing a real object, and further comprising an image capture unit for obtaining image data representing said one of said objects.

7. The optical correlation unit of claim 1, wherein said transform data is obtained by viewing a real object, and further comprising a transform image capture unit for obtaining transform image data representing one of said objects.

8. The optical correlation unit of claim 1, and further comprising a moveable stage for aligning said first object and said second object while said image data and said transform image data are captured, wherein said motion stage has a platform for moving one of said objects with respect to the other.

9. A method for correlating the image of a first object with the image of a second object, comprising the steps of:

obtaining a set of image data representing the image of a first object;

obtaining a set of transform data representing the complex conjugate of the transform image of a second object;

delivering said image data to the electronic input means of a first reflective phase modulating spatial light modulator;

delivering said transform data to the electronic input means of a second reflective phase modulating spatial light modulator;

illuminating the surface of said first spatial light modulator with incident light;

using said first spatial light modulator to modulate said incident light such that a phase encoded version of said image data is reflected from its surface;

directing light reflected from the surface of said first spatial light modulator through a first Fourier transform lens to said second spatial light modulator in the Fourier image plane of said first Fourier transform lens, resulting in a transform of said image data on the reflective surface of said second spatial light modulator;

using said second spatial light modulator to modulate said transform of said image data;

directing light reflected from said second spatial light modulator to a second Fourier transform lens; and capturing the correlation image from said second Fourier transform lens with an image capture device.

10. The method of claim 9, and further comprising the step of tilting said second spatial light modulator to separate said correlation image from other output data.

11. The method of claim 9, and further comprising the step of delivering data representing the correlation image and the image of one of said object to a processor and using said processor to generate a composite image.

12. The method of claim 9, wherein said image data is obtained from a real object, and further comprising the steps of capturing a video image of one of said objects and converting said image to said image data.

13. The method of claim 9, wherein said capturing step is performed in real time with respect to the rest of the correlation steps.

14. The method of claim 9, wherein said transform data is obtained from a real object and further comprising the steps of capturing a Fourier image of one of said objects and converting said image to said transform data.

15. An optical correlation system for providing a correlation image from image data representing a first object and Fourier transform image data representing a second object, comprising:

an image capture unit for obtaining image data representing a first one of said objects;

a transform image capture unit for obtaining transform image data representing a second one of said objects;

a first phase modulating spatial light modulator, having an array of reflective elements and means for receiving said image data as electronic input to each element, which controls the phase modulation of said element;

a coherent light source for illuminating the surface of said first spatial light modulator;

a first Fourier transform lens for receiving light reflected from the surface of said first phase modulating spatial light modulator;

a second phase modulating spatial light modulator, having an array of reflective elements and having means for receiving said transform data as electronic input to each reflective; element for controlling the phase modulation by said element, wherein said second phase modulating spatial light modulator is located at the Fourier image plane of said first Fourier transform lens;

means for directing light reflected from said second spatial light modulator to a Fourier transform lens;

a second Fourier transform lens for receiving said light reflected from said second spatial light modulator; and an image capture device located at the Fourier image plane of said second Fourier transform lens.

16. The optical correlation unit of claim 15, and further comprising a moveable motion stage for aligning said first object and said second object while said image data and said transform image data are captured, wherein said motion stage has a platform for moving one of said objects with respect to the other.

17. The optical correlation unit of claim 15, wherein at least one of said spatial light modulators is a deformable micro-mirror device.

18. The optical correlation unit of claim 15, wherein said spatial light modulator modulates light incident at its surface by adjusting the position of said reflective elements so as to change the path length of incoming light to an image plane.

* * * * *